United States Patent [19]

Adachi et al.

[11] Patent Number: 5,023,453

[45] Date of Patent: Jun. 11, 1991

[54] APPARATUS FOR PREPARATION AND OBSERVATION OF A TOPOGRAPHIC SECTION

[75] Inventors: Tatsuya Adachi; Takashi Kaito, both of Tokyo, Japan

[73] Assignee: Seiko Instruments, Inc., Tokyo, Japan

[21] Appl. No.: 427,537

[22] Filed: Oct. 27, 1989

[30] Foreign Application Priority Data

Nov. 1, 1988 [JP]  Japan .................................. 63-278036

[51] Int. Cl.$^5$ ............................................ H01J 37/00
[52] U.S. Cl. .................................... 250/309; 250/306; 250/307; 250/492.1; 250/492.2; 250/492.3
[58] Field of Search ................ 250/309, 491.1, 492.21, 250/492.2, 492.1, 492.3, 306, 307, 310

[56] References Cited

U.S. PATENT DOCUMENTS

| | | | |
|---|---|---|---|
| 4,088,895 | 5/1978 | Martin | 205/309 |
| 4,451,738 | 5/1984 | Smith | 250/492.21 |
| 4,535,249 | 8/1985 | Reeds | 250/491.1 |
| 4,645,929 | 2/1987 | Criegern et al. | 250/309 |
| 4,687,930 | 8/1987 | Tamura et al. | 250/309 |
| 4,818,872 | 4/1989 | Parker et al. | 250/309 |
| 4,874,947 | 10/1989 | Ward et al. | 250/309 |

*Primary Examiner*—Jack I. Berman
*Assistant Examiner*—Kiet T. Nguyen

*Attorney, Agent, or Firm*—Spensley Horn Jubas & Lubitz

[57] ABSTRACT

An apparatus for effecting preparation and observation of a topographic section in a particular region of a sample. The apparatus includes: a sample chamber for containing a sample, an ion beam irradiation unit mounted in the sample chamber for irradiating the sample with a scanned ion beam to groove the particular region to thereby prepare the topographic section, an electron beam irradiation unit mounted in the sample chamber for irradiating the topographic section with a scanned electron beam, the electron beam irradiation unit being arranged relative to the ion beam irradiation unit such that the electron beam intersects the ion beam at the particular region at an angle not exceeding 90°, a detector for detecting secondary electrons released from the sample upon irradiation with the ion beam and the electron beam, a beam switching circuit operable during the course of the preparation of the topographic section for temporarily switching from the ion beam to the electron beam, and a display connected to the detector and operative in response to the switching for displaying an image of the topographic section based on the detection of the secondary electrons released by the irradiation with the electron beam to thereby temporarily observe the topographic section during the course of the preparation thereof.

4 Claims, 1 Drawing Sheet

APPARATUS FOR PREPARATION AND OBSERVATION OF A TOPOGRAPHIC SECTION

BACKGROUND OF THE INVENTION

The present invention relates to the preparation and observation of topographic sections of semiconductor devices which are highly integrated on a wafer of Si crystal, etc., by an ultra-fine process. The apparatus can be used for evaluation of the LSI fabrication process so as to find problems in the semiconductor device fabrication process.

In order to increase the integration density of large scale integrated circuits (LSI), the individual circuit elements are advantageously made small, and integrated circuits having three dimensional structures have been proposed, including multi-layer lead patterns and trench capacitive elements. As a result, the semiconductor fabrication process becomes more and more complicated and requires several tens to several hundreds of fabrication steps.

Conventionally, a scanning electron microscope is used for topographic surface observation to evaluate the fabrication steps. However, an evaluation of internal structure is necessary for failure analysis of a three dimensional structure. In this regard, since non-destructive surface observation by the scanning electron microscope is not highly effective, observation of topographic sections and profiles has been undertaken by mechanically cutting or scribing a sample. Such mechanical method is not practical for topographic observation of a particular tiny region of interest. However, observation of particular tiny regions of an LSI device is required for failure analysis. For instance, numerous contact holes are formed on a single LSI chip so as to interconnect vertically between multilayered lead patterns, and only one or a few of these is normally defective. Therefore, an analysis of such defective contact hole is quite difficult by conventional mechanical cutting, polishing and etching methods in view of likely positional errors.

FIG. 1 is a top plan view of a contact hole region on an LSI device. This region contains aluminum lead strips 21, a crossing polysilicon lead strip 22 and a contact hole 23 therebetween. In order to undertake topographic observation of the region containing these elements, the sample is cut along a particular line 24 as shown by a chain line in FIG. 1. FIG. 2 is a sectional view taken along this particular line 24. This section contains the upper aluminum lead strip 21, the lower polysilicon lead strip 22 which is electrically connected to the upper aluminum lead strip 21 through contact hole 23, a protective insulating film 25, made of such as silicon nitride, and a silicon substrate 26.

For preparation of the exposed section, the surface of the sample is selectively ion-sputtered by a scanning ion microscopic device to form a crater as defined by chain line 24 of FIG. 1. Then a microscope stage carrying the sample is inclined so as to permit observation of the section thus exposed, as shown in FIG. 2. However, according to such preparation and observation method, in order to observe the section and profile step by step, the sample stage must be angularly displaced several times between a preparation position which is normally horizontal, and an observation position, inclined at 45° to 60° with respect to a horizontal plane, so as to switch between the preparation procedure and the observation procedure for the particular section, thereby causing mechanical error and requiring complicated operations.

Further, since the section cannot be observed in situ during the preparation of the section or during continuous etching of the sample surface, microscopic foreign substances and abnormal micro structures which would be a cause of defects of the contact hole may inadvertently escape the observation.

SUMMARY OF THE INVENTION

It is therefore an object of the present invention to carry out alternate preparation and observation of topographic sections of a sample having micro-fine three dimensional structures so as to eliminate the above-noted drawbacks of the prior art.

The above and other objects are achieved, according to the present invention, by apparatus for the preparation and observation of topographic sections of a sample including an ion beam irradiation unit for irradiating a surface of the sample with a scanning ion beam, an electron beam irradiation unit for irradiating the sample surface with a scanning electron beam, a detector for detecting secondary electrons released from the sample surface upon the irradiation with the respective scanned beams, an image display device for displaying an image based on the output from the detector, and a beam switching device for switching between the scanning ion beam and the scanning electron beam.

The apparatus is constructed such that the ion beam irradiation unit and the electron beam irradiation unit are disposed relative to each other so that their irradiation beam axes intersect each other at an angle not exceeding 90° and they are mounted in the same sample chamber so that both beams irradiate the same spot on the sample surface. The beam switching device alternately switches between the ion beam and the electron beam, and the image display device operates in response to the switching operation of the switching device to selectively display an image of the sample surface and another image of a section of the sample which is prepared by the ion beam irradiation based on the output of the detector.

The preparation and observation apparatus for a sample section can be modified by replacing the electron beam irradiation unit by another ion beam irradiation unit.

In operation, a sample is placed substantially normal to an incident axis of the ion beam, and the ion beam irradiation unit operates as a scanning ion microscope to scan the sample surface with the ion beam to thereby determine a particular spot at which the topographic section is to be prepared. Then, the ion beam intensity is increased and the ion beam is directed to the particular spot to form the desired crater by sputtering. During this material removal operation for preparing the topographic section, the beam switching device is temporarily operated to switch from ion beam irradiation to electron beam irradiation to thereby direct the electron beam obliquely onto a vertical wall of the crater, or groove, to observe it. Thereafter, the beam switching device is again operated to switch back to ion beam irradiation to continue the material removal. By repeating this cycle several times, the preparation of the section is finished.

The electron beam irradiation unit may be replaced by another particle beam irradiation unit such as an ion beam irradiation unit so as to observe the prepared section.

As described above, preparation of the section and observation of the section are effected by separate beam irradiation units independently of each other to thereby enable the observation of the section in situ on a real time basis.

DESCRIPTION OF THE PREFERRED EMBODIMENTS

An embodiment of the present invention will be hereinafter described in detail with reference to the drawings.

Figure 3:
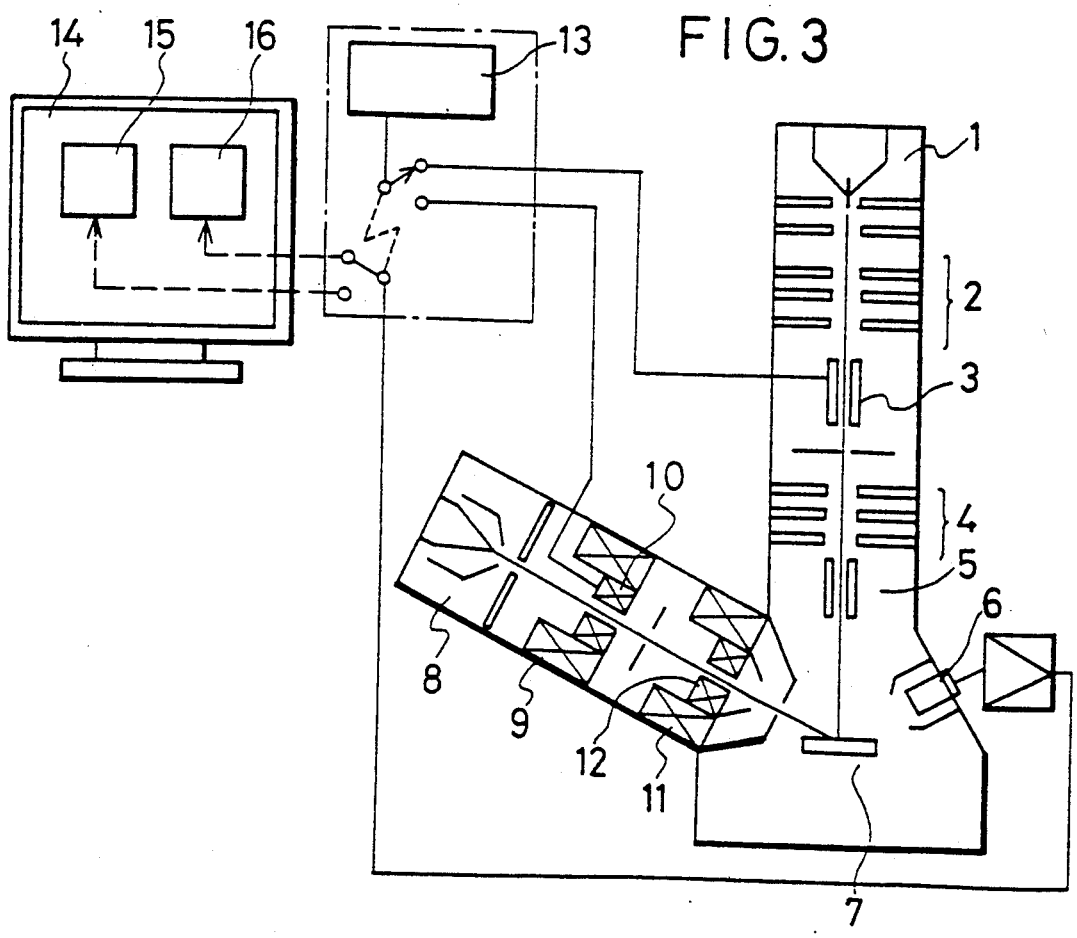
FIG. 3 is a schematic diagram of a preferred embodiment of a preparation and observation apparatus according to the invention.

FIG. 3 is a schematic diagram of the inventive preparation and observation apparatus. The apparatus is composed of a scanning ion beam irradiation unit in the form of a scanning ion microscope, and a scanning electron beam irradiation unit in the form of a scanning electron microscope.

The scanning ion microscope is composed of an ion source 1, a condenser lens 2, a beam blanking electrode 3, an objective lens 4, an XY deflection electrode 5 for scanning an ion beam in X and Y directions along a horizontal plane to irradiate a surface of a sample 7, and a detector 6 for detecting secondary electrons released from the sample upon irradiation of sample 7 by the scanned ion beam. The scanning ion microscope is mounted in a sample chamber.

The scanning electron microscope is composed of an electron gun 8, a condenser lens 9, a beam blanking electrode 10, an objective lens 11, an XY deflection electrode 12 for scanning an electron beam two-dimensionally to irradiate sample 7 with the electron beam, and the common detector 6. The scanning electron microscope is operated to direct a sharply focussed electron beam onto sample 7 so that secondary electrons released from sample 7 are detected by detector 6. The scanning electron microscope is mounted in the sample chamber such that the electron beam axis crosses the ion beam axis at sample 7 at an angle not exceeding 90°.

The secondary electrons released from sample 7 include those induced by ion beam excitation and those induced by electron beam excitation, which cannot be discriminated from each other. Therefore, one of the ion beam and the electron beam must be selected to generate a scanning image of the sample by means of the detection of the secondary electrons. Concurrent irradiation with the ion beam and the electron beam must be avoided to generate a clear scanning image. For this reason, a beam switching device 13 is provided to select one of the ion beam irradiation unit and the electron beam irradiation unit so as to assure generation of a clear scanning image.

Further a display device 14 is provided in the form of a CRT installed in a controlling computer. The display device 14 has a display screen presenting a first display area 15 which displays a topographic section image related to the scanning of the electron beam and a second display area 16 which displays a topographic surface image related to the scanning of the ion beam. The two display areas 15 and 16 are switchable by means of beam switching device 13 concurrently with the switching between the electron and ion beams.

The description will be given hereinbelow for operation of the apparatus of FIG. 3 on the circuit region shown in FIGS. 1 and 2, for instance, involving preparing and observing a particular section taken along the chain line 24 of FIG. 1 which crosses the contact hole 23.

Figure 1:
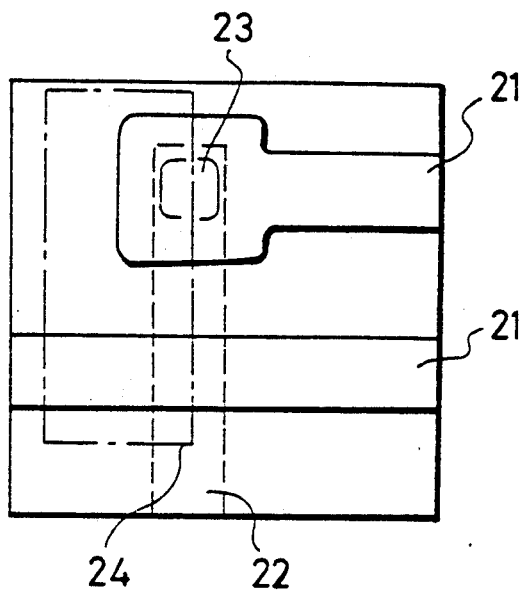
FIG. 1 is a topographic top plan view of the contact hole region on a sample LSI device.
Figure 2:
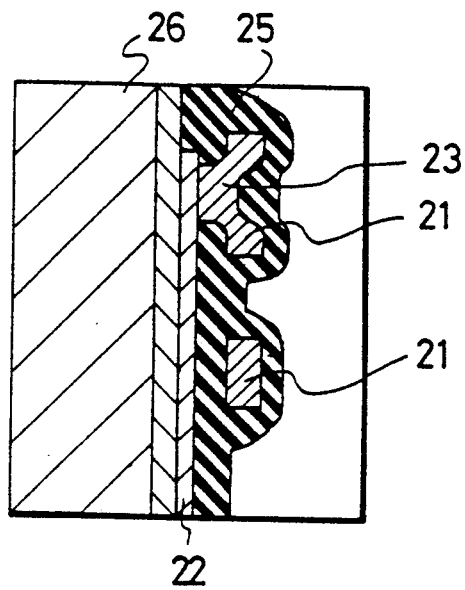
FIG. 2 is a topographic sectional view of the contact hole region shown in FIG. 1.

At first, ion beam irradiation is carried out to effect grooving, or cratering, in the sample surface within the rectangular zone surrounded by chain line 24 of FIG. 1 to thereby expose a vertical section intersecting contact hole 23. Then, device 13 switches from the ion beam to the electron beam so that the electron beam obliquely irradiates the exposed vertical section to thereby permit observation of the same.

In such operation of the apparatus according to the invention, the ion beam irradiation unit and the electron beam irradiation unit are separately provided to independently carry out the preparation of the exposed section and the observation of the same exposed section, respectively. Therefore, during preparation of the topographic section, beam switching device 13 can be selectively operated to switch between the scanning with the ion beam irradiation unit and scanning with the electron beam irradiation unit so that the sample surface image at the base of the groove and the sample section image of the vertical groove edge can be selectively displayed in situ on the corresponding display areas 16 and 15.

These images are produced by intensity-modulating CRT beam as a function of the detected intensity of the secondary electrons. By such switching, the electron-microscopic image of the section is indicated in the display area 15, and the ion-microscopic image of the sample surface during the ion-sputtering is indicated in the other display area 16. By such construction, the observation of a section of a particular spot can be undertaken sequentially during the course of the grooving or the preparation of the section.

Further, a sample stage for supporting a sample can be constructed to permit variation of its inclination angle. By such construction, the ion beam can impinge on the sample at a desired incident angle to thereby permit variation of the angle at which the sample is cut to form the section which can be observed.

According to the present invention, by the above-described construction, during the course of the preparation of a section at a particular spot by means of the ion beam, switching is temporarily effected from the ion beam to the electron beam to effect the observation, thereby allowing recognition of a microscopic foreign substance or an abnormal micro structure which would be the cause of a defect at the particular spot.

Moreover, the apparatus according to the invention does not require complicated operations such as changing of the inclination angle of the sample stage between preparation and observation as opposed to the prior art, thereby effectively avoiding mechanical errors caused by such complicated operations.

This application relates to subject matter disclosed in Japanese Patent Application No. 63-278036, filed Nov. 1, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. An apparatus for effecting preparation and observation of a topographic section in a particular region of a sample, comprising: a sample chamber for containing therein a sample, an ion beam irradiation unit mounted in said sample chamber for irradiating the sample with a scanned ion beam to form a groove in the sample at the particular region, to thereby prepare the topographic section; a particle beam irradiation unit mounted in said sample chamber for irradiating the topographic section of the sample with a scanned particle beam said particle beam irradiation unit being arranged relative to said ion beam irradiation unit such that the particle beam axis intersects the ion beam axis at the particular region at an angle not exceeding 90°; a detector disposed for detecting secondary electrons released from the sample upon irradiation by the ion beam and by the particle beam; beam switching means connected to said units and operable during the course of the preparation of the topographic section for temporarily switching from the ion beam to the particle beam; and display means connected to said detector and having first and second display areas, said display means being operative in response to the switching for displaying in the first display area, an image of the topographic section based on the detection of the secondary electrons released by irradiation of the sample with the particle beam, and for displaying, in the second display area, an image of the surface of the sample based on the detection of the secondary electrons released by irradiation of the sample with the ion beam, to thereby temporarily provide an image of the topographic section and the sample surface during the course of preparation thereof.

2. An apparatus according to claim 1 wherein said particle beam irradiation unit comprises an electron beam irradiation unit for producing a scanned electron beam to irradiate the sample.

3. An apparatus according to claim 1 wherein said particle beam irradiation unit comprises a second ion beam irradiation unit for producing a second scanned ion beam to irradiate the sample.

4. An apparatus according to claim 1 wherein said ion beam irradiation unit is positioned for irradiating the sample in a direction substantially normal to the sample surface, and said particle beam irradiation unit is positioned for irradiating the sample in a direction forming an acute angle to the sample surface.

* * * * *